United States Patent [19]

Umemura et al.

[11] 4,006,167
[45] Feb. 1, 1977

[54] VAPOR PHASE OXIDATION OF UNSATURATED ALIPHATIC HYDROCARBON TO MALEIC ANHYDRIDE USING A CATALYST CONSISTING ESSENTIALLY OF THE OXIDES OF VANADIUM, PHOSPHOROUS, ZIRCONIUM, AND MANGANESE

[75] Inventors: Sumio Umemura; Kyoji Ohdan; Fumihiko Sakai; Yasuo Bando; Harumi Ikezawa, all of Ube, Japan

[73] Assignee: UBE Industries, Ltd., Japan

[22] Filed: June 23, 1975

[21] Appl. No.: 589,518

[30] Foreign Application Priority Data

June 28, 1974 Japan .............................. 49-73255
July 30, 1974 Japan .............................. 49-86609

[52] U.S. Cl. ....................... 260/346.8 A; 252/435; 252/437; 260/533 R; 252/432
[51] Int. Cl.$^2$ ..................................... C07D 307/60
[58] Field of Search ............................ 260/346.8 A

[56] References Cited

UNITED STATES PATENTS

| | | | |
|---|---|---|---|
| 3,156,705 | 11/1964 | Kerr ............................. | 260/346.8 |
| 3,684,741 | 8/1972 | Friedrichsen et al. .......... | 260/346.8 |
| 3,868,393 | 2/1975 | Reuter et al. .................. | 260/346.8 |

FOREIGN PATENTS OR APPLICATIONS

| | | | |
|---|---|---|---|
| 2,133,849 | 1/1972 | France .......................... | 260/346.8 |

Primary Examiner—Natalie Trousof
Assistant Examiner—Bernard Dentz

[57] ABSTRACT

Unsaturated hydrocarbons having 4 to 6 carbon atoms are catalytically oxidized into maleic anhydride at relatively low temperatures in the range of 300° C to 450° C. The catalyst used consists essentially of oxides of vanadium, phosphorus, zirconium, and at least one element selected from manganese, boron, cadmium, silver, bismuth and zinc.

8 Claims, No Drawings

VAPOR PHASE OXIDATION OF UNSATURATED ALIPHATIC HYDROCARBON TO MALEIC ANHYDRIDE USING A CATALYST CONSISTING ESSENTIALLY OF THE OXIDES OF VANADIUM, PHOSPHOROUS, ZIRCONIUM, AND MANGANESE

This invention relates to the synthesis of maleic anhydride by catalytic oxidation of an unsaturated hydrocarbon having 4 to 6 carbon atoms. More particularly, it relates to a process for producing maleic anhydride by contacting in the vapor phase a feed-mixture comprising said unsaturated hydrocarbon and oxygen or on oxygen-containing gas with a catalyst exhibiting an improved activity at a relatively low temperature.

Many proposals have been heretofore put forth for the production of maleic anhydride, which comprise catalytically oxidizing an unsaturated hydrocarbon having four to six carbon atoms such as n-butene, 1,3-butadiene, benzene and cyclopentadiene and a hydrocarbon mixture containing such an unsaturated hydrocarbon having 4 to 6 carbon atoms. Typical processes have been carried out using a catalyst consisting of vanadium, phosphorus and oxygen, or a catalyst consisting of said three components and a metal such as an alkali metal, chromium, titanium, tungsten or molybdenum. These catalysts give relatively attractive conversions and yields when the catalytic oxydation reaction is carried out at a relatively high temperature. An optimum temperature is, in general, approximately 450° C. Such a high temperature is apt to lead to the decomposition of maleic anhydride once produced and the exhalation of phosphorus from the catalyst. Thus, the selectivity to maleic anhydride becomes low and the catalyst life is short.

Japanese Patent Publication 7888/1965 discloses catalysts which consist of a vanadium oxide and a phosphorus oxide, the substantial part of said vanadium having a valency of less than 5. It is referred to that these catalysts optionally contain another metal oxide such as an oxide of titanium, chromium, cobalt, nickel, zinc, zirconium, tin, antimony, bismuth or thorium. Among these catalysts, a catalyst consisting of a vanadium oxide, a phosphorus oxide and a zirconium oxide (the atomic ratio of Zr/V is 1/6) is referred to as possessing the lowest optimum temperature, i.e. 422° C, for the catalytic oxidation of butene-1, and exemplified as giving the yield of 51.8% at the optimum temperature. However, these catalysts including the V—P—Zr oxides catalyst are still not satisfactory because, first, it is required to pretreat vanadium compounds such as vanadium pentoxide and ammonium vanadate with a reducing compound such as oxalic acid for the preparation of vanadium having a valency of less than 5, and secondly, the yield of maleic anhydride is not attractive.

Accordingly, a main object of the present invention is to provide an improved catalyst giving good conversions and yields even at relatively low reaction temperatures.

Another object of the present invention is to provide a process wherein the catalytic oxidation of an unsaturated hydrocarbon having 4 to 6 carbon atoms is carried out at temperatures lower than those in the known processes with the result of good conversions and yields.

These and other objects and advantages of the present invention will become clear from the following description.

In accordance with the present invention, there is provided a process for producing maleic anhydride by catalytic oxidation of an unsaturated hydrocarbon having 4 to 6 carbon atoms, which comprises contacting a feed-gas mixture comprising said unsaturated hydrocarbon and oxygen or an oxygen-containing gas in the vapor phase at a temperature of 300° C to 450° C for a period of 0.1 to 1.8 seconds with a catalyst consisting essentially of oxides of (A) vanadium, (B) phosphorus, (C) zirconium and (D) at least one element selected from the group consisting of manganese, boron, cadmium, silver, bismuth and zinc, in the atomic ratios defined by the following formula

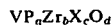

$$VP_aZr_bX_cO_d$$

wherein X is at least one element selected from the above group, and each of $a$, $b$ and $c$ is a positive number indicating an atomic ratio of each of the (B), (C) and (D) to vanadium and falling within the following ranges, $a = 1.0$ to $7.5$, preferably $2.0$ to $5.0$, $b = 1.3$ to $96.0$, preferably $3.0$ to $50$, and $c = 0.05$ to $1.0$, preferably $0.07$ to $0.8$, and $d$ is a positive number satisfying the average valency of the (A), (B), (C) and (D), and being within the range from $8$ to $200$.

The respective components of (A), (B), (C) and (D) should be present in the catalyst in the atomic ratios defined by the above formula. That is, the amount of phosphorus should be such that the atomic ratio of phosphorus to vanadium falls within the range of $1.0$ to $7.5$, preferably $2.0$ to $5.0$. The selectivity to maleic anhydride increases with an increase of the atomic ratio (P/V) of phosphorus to vanadium, but steeply decreases when the atomic ratio (P/V) exceeds approximately $7.5$. The catalyst activity increases gradually with a decrease of the atomic ratio P/V, but the oxidation of the unsaturated hydrocarbon proceeds to an excessive extent and the selectivity to maleic anhydride decreases when the atomic ratio P/V becomes lower than approximately $1.0$. The amount of zirconium should be such that the atomic ratio (Zr/V) of zirconium to vanadium falls within the range of $1.3$ to $96.0$. When the atomic ratio of Zr/V is too small, both the conversion of the unsaturated hydrocarbon and the selectivity to maleic anhydride are low. The optimum reaction temperature becomes low with an increase of the atomic ratio Zr/V, but the yields of maleic anhydride decrease when the atomic ratio Zr/V exceeds approximately $96.0$. The yields of maleic anhydride decrease also when the atomic ratio Zr/V becomes lower than approximately $1.3$.

The amount of manganese, boron, cadmium, silver, bismuth or zinc should be such that the atomic ratio of these elements to vanadium falls within the range of $0.05$ to $1.0$, for the desired yield of maleic anhydride. Among the elements expressed by X set forth above, boron, cadmium, silver, bismuth and zinc are preferable particularly for the conversion of butene-1 because the catalyst provides an increased yield of maleic anhydride. Manganese is preferable particularly for the conversion of 1,3-butadiene for the same reason as set forth above.

The catalyst of the present invention is advantageous over a metal oxide catalyst having a composition similar to that of the present invention but not containing zirconium in the selectivity to maleic anhydrides and the catalyst's mechanical strength.

The manner whereby the catalyst of the present invention is prepared is not critical. The catalyst may be prepared in any known manner provided that the respective component of (A), (B), (C) and (D) are present in the catalyst in amounts such that the catalyst satisfies the above formula. In general, the catalyst is prepared as follows. Compounds each containing at least one component of (A), (B), (C) and (D) are mixed with each other at an elevated temperature, while being stirred, in a liquid medium such as water or an organic solvent, for example, acetone and methyl alcohol to form a solution or a slurry. The order in which the respective component-containing compounds are incorporated in a liquid medium is not critical. For example, a vanadium-containing compound may be first added to a liquid medium, second, a phosphorus-containing compound, third, a zirconium compound and finally a compound containing an element expressed by X set forth above may be incorporated therein. The mixture, i.e. the solution or slurry, so formed is condensed to a paste, kneaded, dried and then calcined usually at 400° C to 600° C. The calcined product is pulverized and shaped into pellets or particles of desired shape and size. Alternatively, the dried mixture may be pulverized and/or shaped into pellets or particles of desired shape and size prior to the calcination. If a promotor element or carrier is used, it is added preferably at a stage prior to the drying of the precipitate or slurry.

The starting compounds may be oxides, acids or salts, or a mixture thereof. Illustrations of the respective component-containing compounds are, for vanadium-containing compounds, vanadium pentoxide, vanadium trioxide, ammonium metavanadate, vanadyl(III) chloride, vanadyl (IV) chloride, vanadyl(V) chloride, vanadium sulfate, vanadium phosphate, vanadyl formate, vanadyl oxalate, metavanadic acid and pyrovanadic acid; for phosphorus-containing compounds, mono-, di- and tri-ammonium phosphate, metaphosphoric acid, triphosphoric acid, pyrophosphoric acid, orthophosphoric acid, phosphorus pentoxide, phosphorus trichloride and ethyl phosphate; for silver-containing compounds, silver oxide, silver phosphate, silver nitrate and silver oxalate; for zirconium-containing compounds, zirconium nitrate, zirconium sulfate, zirconyl chloride, zirconium dioxide and zirconium hydroxide; for bismuth-containing compounds, bismuth nitrate, bismuth oxide, bimuth hydroxide, bismuth hydroxynitrate and bismuth chloride; for manganese-containing compounds, manganese nitrate and manganese oxides; and similarly, for boron-, zinc- and cadmium-containing compounds, nitrates and oxides of these elements.

It is presumed that a part of the catalyst of the invention is in the form of oxides each containing two or more components of the (A), (B), (C) and (D) and another part of the catalyst is in the form of simple oxides each containing a single component.

Unsaturated hydrocarbons having four to six carbon atoms which are used as a starting material in the process of the invention include, for example, n-butene, 1,3-butadiene and cyclopentadiene, and a mixture thereof such as a $C_4$-fraction produced when petroleum naphtha is catalytically cracked, and a spent B-B, i.e. a residue produced when 1,3-butadiene is extracted from the $C_4$-fraction produced.

As a source of oxygen which is used in the catalytic oxidation reaction of the invention, pure oxygen and any oxygen-containing gas may be used. Particularly, air may be advantageously used. A relative proportion of oxygen in the feed-gas mixture is suitably from about 10 to about 200 moles per mole of the unsaturated hydrocarbon. In general, the unsaturated hydrocarbon and oxygen is diluted with an inert diluent gas such as nitrogen in order to avoid the risk of explosion. For example, the unsaturated hydrocarbon is advantageously blended with air in an amount such that the resulting feed mixture contains 2 % by volume or less preferably 0.3 to 1.5% by volume, of the unsaturated hydrocarbon.

Although the optimum reaction temperature varies to some extent depending upon the composition of the catalyst employed, the reaction temperature may be varied within the range 300° C to 450° C, preferably 325° C to 400° C, and more preferably 325° C to 375° C. The contact time may be varied within the range of 0.1 to 1.8 seconds, preferably 0.3 to 1.5 second.

The catalyst may be used alone or in combination with any of the known carriers. As carriers, those which bring favorable effects for the reaction involved, such as silica, alumina, and alumina-silica, which have been deactivated by, e.g. heat-treatment, may suitably be employed. The catalyst may be employed in either a fluidized bed or a fixed bed.

Size and configuration of the catalyst grain are not critical but depend primarily on whether the catalyst is used in a fluidized bed or fixed bed. The catalyst may also be shaped or grained by suitable known methods in order to provide required mechanical strength.

In practice, high yields of maleic anhydride are obtained although the catalytic oxidation of the invention is carried out at a temperature lower than in conventional catalytic oxidation processes, i.e. at a temperature of 325° C to 375° C. Saturated acids such as acetic acid are produced only in trace amount. No detectable amounts of aldehydes are produced.

The invention is further illustrated by the following examples and comparative examples, which are for purposes of illustration only and should not be construed as limiting the invention in any sense. In these examples, conversion and yield were calculated by the following equations.

$$\% \text{ conversion} = \frac{\text{moles UHC consumed}}{\text{moles UHC fed}} \times 100$$

$$\% \text{ yield} = \frac{\text{moles MA produced}}{\text{moles UHC fed}} \times 100$$

where MA is maleic anhydride and UHC is the unsaturated hydrocarbon having 4 to 6 carbon atoms employed. The yield used herein means a one pass yield.

EXAMPLE 1

15.2 g of ammonium metavanadate [$NH_4VO_3$] were added to 800 ml of water with stirring at an elevated temperature to dissolve the ammonium metavanadate in the water. To the aqueous solution, 44.7 g of ammonium primary phosphate [$(NH_4)H_2PO_4$] and then an aqueous 50% solution of 7.4 g manganese nitrate [$Mn(NO_3)_2 \cdot 6H_2O$] were added with stirring. Then, 159.7 g of zirconium dioxide [$ZrO_2$] were added thereto. The mixture was graduated by heating, while being stirred, to obtain a paste.

The paste was kneaded for approximately 1 hour, dried at 110° C for 12 hours and then pulverized into particles of 10 to 20 mesh (Tyler standard sieve). The particles were heated to 500° C at a rate of 100° C/hr. and maintained at that temperature for 10 hours thereby to be calcined. The resulting catalyst had a composition such that the atomic ratio of V : P : Zr : Mn was 1 : 3 : 10 : 0.1.

A feed-mixture of 0.5% by volume of 1,3-butadiene and 99.5% by volume of air was passed through a reactor packed with 20 ml of the above-mentioned catalyst and maintained at 360° C. The contact time was 0.6 second. The conversion of 1,3-butadiene was 100%. The yield of maleic anhydride was 69.1%. The yield of saturated acids was only 1.0% and aldehydes were produced only in trace amounts.

COMPARATIVE EXAMPLE 1

A catalyst was prepared in a manner similar to that in Example 1 wherein the manganese nitrate was not used with all other conditions remaining substantially the same. The catalyst so prepared had the atomic ratio of V : P : Zr = 1 : 3 : 10.

Using the catalyst, 1,3-butadiene was catalytically oxidized in a manner similar to that in Example 1. The conversion of 1,3-butadiene was 100%. The yield of maleic anhydride was 61.7%. The yield of saturated acids was 0.9% and aldehydes were produced in trace amounts.

EXAMPLES 2 and 3

Using the catalyst prepared in Example 1, unsaturated hydrocarbons were catalytically oxidized into maleic anhydride in a manner similar to that in Example 1 wherein cis-butene-2 and butene-1 were separately used instead of 1,3-butadiene. Results are shown in Table I, below.

Table I

| Example No. | Hydrocarbon fed | Conversion (%) | Yield (%) Maleic anhydride | Saturated acids |
|---|---|---|---|---|
| 2 | cis-butene-2 | 100 | 59.0 | 0.9 |
| 3 | butene-1 | 100 | 59.8 | 1.0 |

EXAMPLES 4 through 7 and COMPARATIVE EXAMPLES 2 and 3

Catalysts were prepared in manners similar to that in Example 1 wherein the amounts of ammonium primary phosphate, manganese nitrate and zirconium dioxide were varied with all other conditions remaining substantially the same. The catalysts had the compositions as shown in Table II, below. Using each of the catalysts, 1,3-butadiene was catalytically oxidized in a manner similar to that in Example 1. Results are shown in Table II.

Table II

| Example No. | Catalyst composition (atomic ratio) V | P | Zr | Mn | Conversion (%) | Yield (%) Maleic anhydride | Saturated acids |
|---|---|---|---|---|---|---|---|
| 4 | 1 | 3 | 10 | 0.08 | 100 | 68.8 | 0.8 |
| 5 | 1 | 3 | 10 | 0.7 | 100 | 68.5 | 0.8 |
| 6 | 1 | 3 | 15 | 0.5 | 100 | 67.9 | 0.8 |
| 7 | 1 | 5 | 10 | 0.5 | 100 | 68.3 | 0.7 |
| Com. 2 | 1 | 3 | 0.1 | 0.1 | 85.3 | 47.2 | 0.5 |
| Com. 3 | 1 | 3 | 0 | 0.1 | 81.8 | 42.6 | 0.4 |

COMPARATIVE EXAMPLE 4

A catalyst was prepared in a manner similar to that in Example 1 wherein an excessive amount of ammonium primary phosphate was used with all other conditions remaining substantially the same. The catalyst so prepared had the atomic ratio of V : P : Zr : Mn = 1 : 8 : 10 : 0.5.

Using the catalyst, 1,3-butadiene was catalytically oxidized in a manner similar to that in Example 1. The conversion of 1,3-butadiene was 100%. The yield of maleic anhydride was 57.8%. The yield of saturated acids was 1.2% and aldehydes were produced in trace amounts.

EXAMPLES 8 through 17 and COMPARATIVE EXAMPLES 5 through 9

Catalysts were prepared in a manner similar to that in Example 1 wherein boric acid [$H_3BO_3$], cadmium nitrate [$Cd(NO_3)_2 \cdot 4H_2O$], silver nitrate [$AgNO_3$], bismuth nitrate [$Bi(NO_3)_3 \cdot 5H_2O$] and zinc nitrate [$Zn(NO_3)_2 \cdot 6H_2O$] were separately used instead of manganese nitrate [$Mn(NO_3)_2 \cdot 6H_2O$], and the amounts of the respective compounds were varied. All other conditions substantially remained the same. The resulting catalysts had the atomic ratio as shown in Table III, below.

Using each of the catalysts, butene-1 was catalytically oxidized in a manner similar to that in Example 1. Results are shown in Table III.

Table III

| Example No. | Catalyst Composition (atomic ratio) V | P | Zr | B | Cd | Ag | Bi | Zn | Conversion (%) | Yield (%) Maleic anhydride | Saturated acids |
|---|---|---|---|---|---|---|---|---|---|---|---|
| 8 | 1 | 3 | 10 | 0.5 | — | — | — | — | 100 | 56.8 | 1.0 |
| Com. 5 | 1 | 3 | 10 | 2 | — | — | — | — | 96.9 | 52.3 | 0.8 |
| 9 | 1 | 3 | 10 | — | 0.5 | — | — | — | 100 | 57.0 | 0.8 |
| 10 | 1 | 3 | 10 | — | — | 0.5 | — | — | 100 | 57.3 | 0.9 |

Table III-continued

| Example No. | V | P | Zr | B | Cd | Ag | Bi | Zn | Conversion (%) | Yield (%) Maleic anhydride | Yield (%) Saturated acids |
|---|---|---|---|---|---|---|---|---|---|---|---|
| 11 | 1 | 3 | 10 | — | — | — | 0.08 | — | 100 | 57.8 | 0.8 |
| 12 | 1 | 3 | 10 | — | — | — | 0.5 | — | 100 | 57.5 | 1.2 |
| 13 | 1 | 3 | 10 | — | — | — | 0.7 | — | 100 | 56.9 | 0.9 |
| Com. 6 | 1 | 3 | 10 | — | — | — | 2 | — | 100 | 52.3 | 0.8 |
| 14 | 1 | 3 | 15 | — | — | — | 0.5 | — | 100 | 57.3 | 1.0 |
| 15 | 1 | 5 | 10 | — | — | — | 0.5 | — | 100 | 56.7 | 0.7 |
| 16 | 1 | 2 | 5 | — | — | — | 0.5 | — | 100 | 56.5 | Trace |
| Com. 7 | 1 | 10 | 10 | — | — | — | 0.5 | — | 91.7 | 49.1 | 0.8 |
| 17 | 1 | 3 | 10 | — | — | — | — | 0.5 | 100 | 57.1 | 0.9 |
| Com. 8 | 1 | 3 | 10 | — | — | — | — | 2 | 100 | 51.8 | 0.7 |
| Com. 9 | 1 | 3 | 10 | — | — | — | — | — | 100 | 53.3 | 0.8 |

EXAMPLE 18 and 19

Using the catalyst prepared in Example 12, unsaturated hydrocarbons were catalytically oxidized into maleic anhydride in a manner similar to that in Example 1 wherein 1,3-butadiene and cis-butene-2 were separately used. Results are shown in Table IV.

Table IV

| Example No. | Hydrocarbon fed | Conversion (%) | Yield (%) Maleic anhydride | Yield (%) Saturated acids |
|---|---|---|---|---|
| 18 | 1,3-butadiene | 100 | 67.0 | 0.8 |
| 19 | cis-butene-2 | 100 | 56.8 | 1.1 |

What we claim is:

1. A process for producing maleic anhydride by catalytic oxidation of an unsaturated aliphatic hydrocarbon having 4 to 6 carbon atoms, which comprises contacting a feed-gas mixture comprising said unsaturated aliphatic hydrocarbon and oxygen or an oxygen-containing gas in the vapor phase at a temperature of 300° C to 450° C for a period of 0.1 to 1.8 seconds with a catalyst consisting essentially of oxides of (A) vanadium, (B) phosphorus, (C) zirconium and (D) manganese in the atomic ratios defined by the formula

$VP_aZr_bMn_cO_d$ wherein each of $a$, $b$ and $c$ is a positive number indicating an atomic ratio of each of the aforesaid (B), (C) and (D) to vanadium and falling within the following ranges, $a = 1.0$ to $7.5$, $b = 1.3$ to $96.0$ and $c = 0.05$ to $1.0$, and $d$ is a positive number satisfying the average valency of the (A), (B), (C) and (D), and being within the range of 8 to 200.

2. A process according to claim 1 wherein said catalyst is the calcined residue of a mixture formed by mixing in an aqueous system compounds each containing at least one component of the (A), (B), (C) and (D), said compounds being in the form of oxide, acid, salt or a mixture thereof.

3. A process according to claim 1 wherein $a$, $b$ and $c$ are positive numbers falling within the range of 2.0 to 5.0, 3.0 to 50 and 0.07 to 0.8, respectively.

4. A process according to claim 1 wherein said unsaturated aliphatic hydrocarbon having 4 to 6 carbon atoms is selected from the group consisting of butene-1, 1,3-butadiene, cis-butene-2 and a mixture thereof.

5. A process according to claim 1 wherein said aliphatic unsaturated hydrocarbon is 1,3-butadiene.

6. A process according to claim 1 wherein said oxygen-containing gas is air.

7. A process according to claim 1 wherein said oxidation reaction is carried out at a temperature of 325° C to 400° C and at a contact time of 0.3 to 1.5 second.

8. A process according to claim 7 wherein said temperature is within the range of 325° C to 375° C.

* * * * *